US011938002B2

(12) United States Patent
Hunt et al.

(10) Patent No.: US 11,938,002 B2
(45) Date of Patent: *Mar. 26, 2024

(54) CONTROL OF WOUND CLOSURE AND FLUID REMOVAL MANAGEMENT IN WOUND THERAPY

(71) Applicant: Smith & Nephew, Inc., Memphis, TN (US)

(72) Inventors: Allan Kenneth Frazer Grugeon Hunt, Hull (GB); William Joseph Jaecklein, Saint Petersburg, FL (US); Felix Clarence Quintanar, Hull (GB)

(73) Assignee: Smith & Nephew, Inc., Memphis, TN (US)

( * ) Notice: Subject to any disclaimer, the term of this patent is extended or adjusted under 35 U.S.C. 154(b) by 62 days.

This patent is subject to a terminal disclaimer.

(21) Appl. No.: 17/870,718

(22) Filed: Jul. 21, 2022

(65) Prior Publication Data

US 2023/0017606 A1 Jan. 19, 2023

Related U.S. Application Data

(63) Continuation of application No. 16/616,823, filed as application No. PCT/US2018/037165 on Jun. 12, 2018, now Pat. No. 11,395,873.

(Continued)

(51) Int. Cl.
*A61F 13/05* (2024.01)
*A61M 1/00* (2006.01)

(52) U.S. Cl.
CPC ............... *A61F 13/05* (2024.01); *A61M 1/73* (2021.05); *A61M 1/90* (2021.05); *A61M 1/96* (2021.05);

(Continued)

(58) Field of Classification Search
CPC ............ A61M 1/90; A61M 2205/3331; A61M 2205/50; A61M 1/73; A61M 2205/3379;

(Continued)

(56) References Cited

U.S. PATENT DOCUMENTS 3,194,239 A 7/1965 Sullivan et al.
3,789,851 A 2/1974 LeVeen (Continued)

FOREIGN PATENT DOCUMENTS

AU 2012261793 B2 11/2014
AU 2013206230 B2 5/2016

(Continued)

OTHER PUBLICATIONS

"Definition of 3D Printer," American Heritage Dictionary of the English Language, Fifth Edition, accessed on Feb. 22, 2018 from URL: https://www.thefreedictionary.com, 2016, 1 page.

(Continued)

*Primary Examiner* — Kai H Weng
*Assistant Examiner* — Nhu Q. Tran
(74) *Attorney, Agent, or Firm* — Knobbe, Martens, Olson & Bear, LLP

(57) ABSTRACT

Embodiments of negative pressure wound therapy systems and methods for operating the systems are disclosed. In one embodiment, a negative pressure source can provide negative pressure via a fluid flow path to a wound dressing comprising a stabilizing structure. The stabilizing structure can be inserted into a wound and collapse upon application of negative pressure to the wound when the stabilizing structure is positioned in the wound. A controller can in turn determine a measure of collapse of the stabilizing structure from a pressure in the fluid flow path while the negative pressure source maintains a magnitude of the pressure in the fluid flow path within a negative pressure range. The con- (Continued)

troller can output an indication responsive to the measure of collapse.

20 Claims, 9 Drawing Sheets

Related U.S. Application Data

(60) Provisional application No. 62/519,790, filed on Jun. 14, 2017.

(52) U.S. Cl.
CPC ............ *A61M 1/982* (2021.05); *A61M 1/985* (2021.05); *A61M 2205/3331* (2013.01); *A61M 2205/35* (2013.01); *A61M 2205/50* (2013.01)

(58) Field of Classification Search
CPC ....... A61M 2205/35; A61M 2205/3584; A61F 13/00068; A61F 13/0216; A61F 2013/0094
See application file for complete search history.

(56) References Cited

U.S. PATENT DOCUMENTS

| | | | |
|---|---|---|---|
| 4,467,805 A | 8/1984 | Fukuda |
| 4,608,041 A | 8/1986 | Nielsen |
| 4,699,134 A | 10/1987 | Samuelsen |
| 4,815,468 A | 3/1989 | Annand |
| 5,176,663 A | 1/1993 | Svedman et al. |
| 5,264,218 A | 11/1993 | Rogozinski |
| 5,376,067 A | 12/1994 | Daneshvar |
| 5,409,472 A | 4/1995 | Rawlings et al. |
| 5,415,715 A | 5/1995 | Delage et al. |
| 5,423,857 A | 6/1995 | Rosenman et al. |
| 5,512,041 A | 4/1996 | Bogart |
| 5,562,107 A | 10/1996 | Lavender et al. |
| 5,584,859 A | 12/1996 | Brotz |
| 5,636,643 A | 6/1997 | Argenta et al. |
| 5,695,777 A | 12/1997 | Donovan et al. |
| 6,176,868 B1 | 1/2001 | Detour |
| 6,503,208 B1 | 1/2003 | Skovlund |
| 6,548,727 B1 | 4/2003 | Swenson |
| 6,566,575 B1 | 5/2003 | Stickels et al. |
| 6,685,681 B2 | 2/2004 | Lockwood et al. |
| 6,770,794 B2 | 8/2004 | Fleischmann |
| 6,787,682 B2 | 9/2004 | Gilman |
| 6,977,323 B1 | 12/2005 | Swenson |
| 7,004,915 B2 | 2/2006 | Boynton et al. |
| 7,144,390 B1 | 12/2006 | Hannigan et al. |
| 7,315,183 B2 | 1/2008 | Hinterscher |
| 7,351,250 B2 | 4/2008 | Zamierowski |
| 7,361,184 B2 | 4/2008 | Joshi |
| 7,438,705 B2 | 10/2008 | Karpowicz et al. |
| 7,494,482 B2 | 2/2009 | Orgill et al. |
| 7,615,036 B2 | 11/2009 | Joshi et al. |
| 7,622,629 B2 | 11/2009 | Aali |
| 7,625,362 B2 | 12/2009 | Boehringer et al. |
| 7,683,667 B2 | 3/2010 | Kim |
| 7,700,819 B2 | 4/2010 | Ambrosio et al. |
| 7,754,937 B2 | 7/2010 | Boehringer et al. |
| 7,779,625 B2 | 8/2010 | Joshi et al. |
| 7,815,616 B2 | 10/2010 | Boehringer et al. |
| 7,846,141 B2 | 12/2010 | Weston |
| 7,857,806 B2 | 12/2010 | Karpowicz et al. |
| 7,863,495 B2 | 1/2011 | Aali |
| 7,892,181 B2 | 2/2011 | Christensen et al. |
| 7,896,856 B2 | 3/2011 | Petrosenko et al. |
| 7,909,805 B2 | 3/2011 | Weston |
| 7,910,789 B2 | 3/2011 | Sinyagin |
| 7,931,774 B2 | 4/2011 | Hall et al. |
| 7,942,866 B2 | 5/2011 | Radl et al. |
| 7,951,124 B2 | 5/2011 | Boehringer et al. |
| 7,964,766 B2 | 6/2011 | Blott et al. |
| 7,976,519 B2 | 7/2011 | Bubb et al. |
| 7,976,524 B2 | 7/2011 | Kudo et al. |
| 8,030,534 B2 | 10/2011 | Radl et al. |
| 8,057,447 B2 | 11/2011 | Olson et al. |
| 8,062,331 B2 | 11/2011 | Zamierowski |
| 8,067,662 B2 | 11/2011 | Aali et al. |
| 8,070,773 B2 | 12/2011 | Zamierowski |
| 8,114,126 B2 | 2/2012 | Heaton et al. |
| 8,123,781 B2 | 2/2012 | Zamierowski |
| 8,142,419 B2 | 3/2012 | Heaton et al. |
| 8,172,816 B2 | 5/2012 | Kazala, Jr. et al. |
| 8,187,237 B2 | 5/2012 | Seegert |
| 8,188,331 B2 | 5/2012 | Barta et al. |
| 8,197,467 B2 | 6/2012 | Heaton et al. |
| 8,207,392 B2 | 6/2012 | Haggstrom et al. |
| 8,235,955 B2 | 8/2012 | Blott et al. |
| 8,246,590 B2 | 8/2012 | Hu et al. |
| 8,257,328 B2 | 9/2012 | Augustine et al. |
| 8,273,105 B2 | 9/2012 | Cohen et al. |
| 8,328,776 B2 | 12/2012 | Kelch et al. |
| 8,337,411 B2 | 12/2012 | Nishtala et al. |
| 8,353,931 B2 | 1/2013 | Stopek et al. |
| 8,357,131 B2 | 1/2013 | Olson |
| 8,366,692 B2 | 2/2013 | Weston et al. |
| 8,376,972 B2 | 2/2013 | Fleischmann |
| 8,430,867 B2 | 4/2013 | Robinson et al. |
| 8,447,375 B2 | 5/2013 | Shuler |
| 8,454,990 B2 | 6/2013 | Canada et al. |
| 8,460,257 B2 | 6/2013 | Locke et al. |
| 8,481,804 B2 | 7/2013 | Timothy |
| 8,486,032 B2 | 7/2013 | Seegert et al. |
| 8,500,776 B2 | 8/2013 | Ebner |
| 8,608,776 B2 | 12/2013 | Coward et al. |
| 8,632,523 B2 | 1/2014 | Eriksson et al. |
| 8,673,992 B2 | 3/2014 | Eckstein et al. |
| 8,679,080 B2 | 3/2014 | Kazala, Jr. et al. |
| 8,679,153 B2 | 3/2014 | Dennis |
| 8,680,360 B2 | 3/2014 | Greener et al. |
| 8,708,984 B2 | 4/2014 | Robinson et al. |
| 8,721,629 B2 | 5/2014 | Hardman et al. |
| 8,746,662 B2 | 6/2014 | Poppe |
| 8,764,732 B2 | 7/2014 | Hartwell |
| 8,791,315 B2 | 7/2014 | Lattimore et al. |
| 8,791,316 B2 | 7/2014 | Greener |
| 8,802,916 B2 | 8/2014 | Griffey et al. |
| 8,821,535 B2 | 9/2014 | Greener |
| 8,945,030 B2 | 2/2015 | Weston |
| 9,044,579 B2 | 6/2015 | Blott et al. |
| 9,061,095 B2 | 6/2015 | Adie et al. |
| 9,180,231 B2 | 11/2015 | Greener |
| 9,408,755 B2 | 8/2016 | Larsson |
| 9,421,132 B2 | 8/2016 | Dunn |
| 9,655,807 B2 | 5/2017 | Locke et al. |
| 9,849,023 B2 | 12/2017 | Hall et al. |
| 10,143,485 B2 | 12/2018 | Locke et al. |
| 11,123,476 B2 | 9/2021 | Hunt et al. |
| 2001/0034499 A1 | 10/2001 | Sessions et al. |
| 2002/0077661 A1 | 6/2002 | Saadat |
| 2002/0161346 A1 | 10/2002 | Lockwood et al. |
| 2004/0162512 A1 | 8/2004 | Liedtke et al. |
| 2004/0267312 A1 | 12/2004 | Kanner et al. |
| 2005/0142331 A1 | 6/2005 | Anderson et al. |
| 2005/0267424 A1 | 12/2005 | Eriksson et al. |
| 2006/0020269 A1 | 1/2006 | Cheng |
| 2006/0058842 A1 | 3/2006 | Wilke et al. |
| 2006/0069357 A1 | 3/2006 | Marasco |
| 2006/0155260 A1 | 7/2006 | Blott et al. |
| 2006/0217795 A1 | 9/2006 | Besselink et al. |
| 2006/0271018 A1 | 11/2006 | Korf |
| 2007/0038172 A1 | 2/2007 | Zamierowski |
| 2007/0052144 A1 | 3/2007 | Knirck et al. |
| 2007/0104941 A1 | 5/2007 | Kameda et al. |
| 2007/0118096 A1 | 5/2007 | Smith et al. |
| 2007/0123973 A1 | 5/2007 | Roth et al. |
| 2007/0129660 A1 | 6/2007 | McLeod et al. |
| 2007/0149910 A1 | 6/2007 | Zocher |
| 2007/0185463 A1 | 8/2007 | Mulligan |
| 2007/0213597 A1 | 9/2007 | Wooster |
| 2007/0282309 A1 | 12/2007 | Bengtson et al. |

(56) References Cited

U.S. PATENT DOCUMENTS

| | | |
|---|---|---|
| 2008/0041401 A1 | 2/2008 | Casola et al. |
| 2008/0108977 A1 | 5/2008 | Heaton et al. |
| 2008/0215020 A1 | 9/2008 | Reeves et al. |
| 2008/0243096 A1 | 10/2008 | Svedman |
| 2008/0275409 A1 | 11/2008 | Kane et al. |
| 2008/0306456 A1 | 12/2008 | Riesinger |
| 2009/0005716 A1 | 1/2009 | Abuzaina et al. |
| 2009/0099519 A1 | 4/2009 | Kaplan |
| 2009/0105670 A1 | 4/2009 | Bentley et al. |
| 2009/0204423 A1 | 8/2009 | Degheest et al. |
| 2009/0312685 A1 | 12/2009 | Olsen et al. |
| 2010/0022990 A1 | 1/2010 | Karpowicz et al. |
| 2010/0047324 A1 | 2/2010 | Fritz et al. |
| 2010/0081983 A1 | 4/2010 | Zocher et al. |
| 2010/0101583 A1 | 4/2010 | Chen et al. |
| 2010/0137775 A1 | 6/2010 | Hu et al. |
| 2010/0150991 A1 | 6/2010 | Bernstein |
| 2010/0160874 A1 | 6/2010 | Robinson et al. |
| 2010/0179515 A1 | 7/2010 | Swain et al. |
| 2010/0198128 A1 | 8/2010 | Turnlund et al. |
| 2010/0262106 A1 | 10/2010 | Hartwell |
| 2010/0280468 A1 | 11/2010 | Haggstrom et al. |
| 2010/0298792 A1 | 11/2010 | Weston et al. |
| 2010/0312159 A1 | 12/2010 | Aali et al. |
| 2011/0021965 A1 | 1/2011 | Karp et al. |
| 2011/0022082 A1 | 1/2011 | Burke et al. |
| 2011/0059291 A1 | 3/2011 | Boyce et al. |
| 2011/0066096 A1 | 3/2011 | Svedman |
| 2011/0077605 A1 | 3/2011 | Karpowicz et al. |
| 2011/0082480 A1 | 4/2011 | Viola |
| 2011/0092958 A1 | 4/2011 | Jacobs |
| 2011/0110996 A1 | 5/2011 | Schoenberger et al. |
| 2011/0112458 A1 | 5/2011 | Holm et al. |
| 2011/0178451 A1 | 7/2011 | Robinson et al. |
| 2011/0224631 A1 | 9/2011 | Simmons et al. |
| 2011/0224632 A1 | 9/2011 | Zimnitsky et al. |
| 2011/0224634 A1 | 9/2011 | Locke et al. |
| 2011/0264138 A1 | 10/2011 | Avelar et al. |
| 2011/0270301 A1 | 11/2011 | Cornet et al. |
| 2011/0305736 A1 | 12/2011 | Wieland et al. |
| 2012/0016321 A1 | 1/2012 | Wu et al. |
| 2012/0029455 A1 | 2/2012 | Perez-Foullerat et al. |
| 2012/0059412 A1 | 3/2012 | Fleischmann |
| 2012/0130327 A1 | 5/2012 | Marquez |
| 2012/0136326 A1 | 5/2012 | Croizat et al. |
| 2012/0136328 A1 | 5/2012 | Johannison et al. |
| 2012/0143113 A1 | 6/2012 | Robinson et al. |
| 2012/0172926 A1 | 7/2012 | Hotter |
| 2012/0191132 A1 | 7/2012 | Sargeant |
| 2012/0209226 A1 | 8/2012 | Simmons et al. |
| 2012/0209227 A1 | 8/2012 | Dunn |
| 2012/0253302 A1 | 10/2012 | Corley |
| 2012/0259274 A1 | 10/2012 | Hutchinson et al. |
| 2013/0023719 A1 | 1/2013 | Bennett |
| 2013/0023842 A1 | 1/2013 | Song |
| 2013/0150813 A1 | 6/2013 | Gordon et al. |
| 2013/0190705 A1 | 7/2013 | Vess et al. |
| 2013/0197457 A1 | 8/2013 | Kazala, Jr. et al. |
| 2013/0204213 A1 | 8/2013 | Heagle et al. |
| 2013/0245527 A1 | 9/2013 | Croizat et al. |
| 2013/0325142 A1 | 12/2013 | Hunter et al. |
| 2013/0331757 A1 | 12/2013 | Belson |
| 2014/0094730 A1 | 4/2014 | Greener et al. |
| 2014/0163415 A1 | 6/2014 | Zaiken et al. |
| 2014/0249495 A1 | 9/2014 | Mumby et al. |
| 2015/0065968 A1 | 3/2015 | Sealy et al. |
| 2015/0119837 A1 | 4/2015 | Thompson, Jr. et al. |
| 2015/0157758 A1 | 6/2015 | Blucher et al. |
| 2015/0190288 A1 | 7/2015 | Dunn et al. |
| 2015/0196431 A1 | 7/2015 | Dunn et al. |
| 2015/0216732 A1 | 8/2015 | Hartwell et al. |
| 2015/0320602 A1 | 11/2015 | Locke et al. |
| 2015/0328399 A1 | 11/2015 | Heitmeier et al. |
| 2015/0374561 A1 | 12/2015 | Hubbard, Jr. et al. |
| 2016/0144085 A1 | 5/2016 | Melin et al. |
| 2016/0184496 A1 | 6/2016 | Jaecklein et al. |
| 2017/0065751 A1 | 3/2017 | Toth |
| 2017/0281838 A1 | 10/2017 | Dunn |
| 2018/0228945 A1 | 8/2018 | Guirguis et al. |
| 2018/0229014 A1 | 8/2018 | Guirguis et al. |
| 2020/0289723 A1 | 9/2020 | Gregory et al. |

FOREIGN PATENT DOCUMENTS

| | | |
|---|---|---|
| CN | 101112326 A | 1/2008 |
| CN | 101744688 A | 6/2010 |
| CN | 201519362 U | 7/2010 |
| CN | 102038575 A | 5/2011 |
| CN | 202568632 U | 12/2012 |
| CN | 103071197 A | 5/2013 |
| CN | 203408163 U | 1/2014 |
| DE | 2949920 A1 | 3/1981 |
| EP | 1320342 A1 | 6/2003 |
| EP | 2279016 A1 | 2/2011 |
| EP | 2567717 A1 | 3/2013 |
| GB | 2389794 A | 12/2003 |
| GB | 2423019 A | 8/2006 |
| GB | 2489947 A | 10/2012 |
| GB | 2496310 A | 5/2013 |
| JP | S6257560 A | 3/1987 |
| JP | 2012105840 A | 6/2012 |
| RU | 62504 U1 | 4/2007 |
| SU | 1818103 A1 | 5/1993 |
| WO | WO-0185248 A1 | 11/2001 |
| WO | WO-0189392 A2 | 11/2001 |
| WO | WO-0205737 A1 | 1/2002 |
| WO | WO-03003948 A1 | 1/2003 |
| WO | WO-03049598 A2 | 6/2003 |
| WO | WO-2005046761 A1 | 5/2005 |
| WO | WO-2005105174 A1 | 11/2005 |
| WO | WO-2006046060 A2 | 5/2006 |
| WO | WO-2008027449 A2 | 3/2008 |
| WO | WO-2008064502 A1 | 6/2008 |
| WO | WO-2008104609 A1 | 9/2008 |
| WO | WO-2009112062 A1 | 9/2009 |
| WO | WO-2010033725 A2 | 3/2010 |
| WO | WO-2010097570 A1 | 9/2010 |
| WO | WO-2011023384 A1 | 3/2011 |
| WO | WO-2012082716 A2 | 6/2012 |
| WO | WO-2012082876 A1 | 6/2012 |
| WO | WO-2012136707 A1 | 10/2012 |
| WO | WO-2012142473 A1 | 10/2012 |
| WO | WO-2013012381 A1 | 1/2013 |
| WO | WO-2013043258 A1 | 3/2013 |
| WO | WO-2013066694 A2 | 5/2013 |
| WO | WO-2013071243 A2 | 5/2013 |
| WO | WO-2013076450 A1 | 5/2013 |
| WO | WO-2013079947 A1 | 6/2013 |
| WO | WO-2013175309 A1 | 11/2013 |
| WO | WO-2013175310 A2 | 11/2013 |
| WO | WO-2014013348 A2 | 1/2014 |
| WO | WO-2014014871 A1 | 1/2014 |
| WO | WO-2014014922 A1 | 1/2014 |
| WO | WO-2014140578 A1 | 9/2014 |
| WO | WO-2014151930 A2 | 9/2014 |
| WO | WO-2014158526 A1 | 10/2014 |
| WO | WO-2014165275 A1 | 10/2014 |
| WO | WO-2014178945 A1 | 11/2014 |
| WO | WO-2014194786 A1 | 12/2014 |
| WO | WO-2015008054 A1 | 1/2015 |
| WO | WO-2015023515 A1 | 2/2015 |
| WO | WO-2015061352 A2 | 4/2015 |
| WO | WO-2015109359 A1 | 7/2015 |
| WO | WO-2015110409 A1 | 7/2015 |
| WO | WO-2015110410 A1 | 7/2015 |
| WO | WO-2015169637 A1 | 11/2015 |
| WO | WO-2015193257 A1 | 12/2015 |
| WO | WO-2016018448 A1 | 2/2016 |
| WO | WO-2016129816 A1 | 8/2016 |
| WO | WO-2016176513 A1 | 11/2016 |
| WO | WO-2016179245 A1 | 11/2016 |
| WO | WO-2017106576 A1 | 6/2017 |
| WO | WO-2018038665 A1 | 3/2018 |
| WO | WO-2018041805 A1 | 3/2018 |

(56) References Cited

FOREIGN PATENT DOCUMENTS

| WO | WO-2018044944 A1 | 3/2018 |
| WO | WO-2018044949 A1 | 3/2018 |
| WO | WO-2018085457 A1 | 5/2018 |
| WO | WO-2018140386 A2 | 8/2018 |
| WO | WO-2018148017 A1 | 8/2018 |
| WO | WO-2018148487 A1 | 8/2018 |
| WO | WO-2018231874 A1 | 12/2018 |
| WO | WO-2018237206 A2 | 12/2018 |

OTHER PUBLICATIONS

"Definition of Adhere," The Free Dictionary, accessed on Mar. 23, 2017 from http://www.thefreedictionary.com/adhere, 6 pages.

"Definition of Oculiform," Webster's Revised Unabridged Dictionary, accessed from The Free Dictionary on May 30, 2018 from URL: https://www.thefreedictionary.com/Oculiform, 1913, 1 page.

"Definition of Throughout," Merriam-Webster Dictionary, accessed on Aug. 29, 2017 from https://www.merriam-webster.com/dictionary/throughout, 11 pages.

Hougaard, et al., "The Open Abdomen: Temporary Closure with a Modified Negative Pressure Therapy Technique," International Wound Journal, ISSN 1742-4801, 2014, pp. 13-16.

International Preliminary Report on Patentability for Application No. PCT/US2018/037165, dated Dec. 17, 2019, 7 pages.

International Preliminary Report on Patentability for Application No. PCT/US2018/037169, dated Dec. 26, 2019, 12 pages.

International Search Report and Written Opinion for PCT Application No. PCT/US2018/037165, dated Aug. 31, 2018, 10 pages.

International Search Report and Written Opinion for Application No. PCT/US2018/037169, dated Nov. 23, 2018, 23 pages.

Invitation to Pay Additional Fees and Partial Search Report for Application No. PCT/US2018/037169, dated Sep. 25, 2018, 17 pages.

Kapischke M., et al., "Self-Fixating Mesh for the Lichtenstein Procedure-a Prestudy," Langenbeck's Arch Surg, 2010, vol. 395, pp. 317-322.

CONTROL OF WOUND CLOSURE AND FLUID REMOVAL MANAGEMENT IN WOUND THERAPY

CROSS-REFERENCE TO RELATED APPLICATIONS

This application is a continuation of U.S. application Ser. No. 16/616,823, filed Nov. 25, 2019, which is a U.S. national stage application of International Patent Application No. PCT/US2018/037165, filed Jun. 12, 2018, which claims priority to U.S. Provisional Application No. 62/519,790, filed Jun. 14, 2017; the disclosures of which are hereby incorporated by reference in their entirety.

BACKGROUND

Embodiments of the present disclosure relate to methods and apparatuses for dressing and providing therapy to a wound. In particular, but without limitation, embodiments disclosed herein relate to negative pressure therapy devices, methods for controlling the operation of topical negative pressure (TNP) systems, and methods of using TNP systems.

SUMMARY

In some embodiments, a wound therapy apparatus is disclosed. The wound therapy apparatus includes: a negative pressure source configured to provide negative pressure via a fluid flow path to a wound dressing comprising a stabilizing structure, the stabilizing structure being configured to be inserted into a wound and collapse upon application of negative pressure to the wound when the stabilizing structure is positioned in the wound; a sensor configured to detect pressure in the fluid flow path; and a controller. The controller is configured to: determine a measure of collapse of the stabilizing structure from the pressure in the fluid flow path while the negative pressure source maintains a magnitude of the pressure in the fluid flow path within a negative pressure range, and output an indication responsive to the measure of collapse.

The wound therapy apparatus of the preceding paragraph can include one or more of the following features: The controller is configured to determine the measure of collapse from a change in the magnitude of the pressure in the fluid flow path over time. The controller is further configured to determine the measure of collapse from a comparison of the magnitude of the pressure in the fluid flow path over time to a pressure change pattern. The pressure change pattern is indicative of one or more of: (i) pressure magnitude in the fluid flow path when the stabilizing structure is fully collapsed, (ii) pressure magnitude in the fluid flow path when the stabilizing structure is partially collapsed, or (iii) pressure magnitude in the fluid flow path when the stabilizing structure is not collapsed. The measure of collapse comprises a rate of collapse of the stabilizing structure. The controller is further configured to detect that a suture burst or failed from the pressure in the fluid flow path, the suture being proximate to the wound dressing. The controller is configured to output the indication to (i) activate or deactivate the negative pressure source, (ii) activate or deactivate an alarm, (iii) increase or decrease a target negative pressure provided by the negative pressure source, or (iv) release negative pressure in the fluid flow path. The controller is configured to output the indication to control activation and deactivation of the negative pressure source for a time period according to a target level of collapse of the stabilizing structure rather than to control activation and deactivation of the negative pressure source to adjust the magnitude of the pressure in the fluid flow path to target a predetermined negative pressure threshold. The time period is at least 1 minutes, 5 minutes, 10 minutes, 30 minutes, 1 hour, or 5 hours. The controller is configured to output the indication for presentation to a user or storage in a memory device. The controller is further configured to store, in a memory device, device usage data in association with the indication, and the device usage data comprises one or more of a pressure level, an alarm, an exudate level, an event log, and an operation use time. The controller is further configured to determine whether the wound dressing comprises the stabilizing structure from the pressure in the fluid flow path. The sensor is configured to detect the pressure in the fluid flow path at the wound dressing, in one or more lumens of the fluid flow path, or at an inlet of the negative pressure source. The negative pressure source is configured to perform negative pressure therapy when the magnitude of the pressure in the fluid flow path is maintained within the negative pressure range.

In some embodiments, a method of operating a wound therapy apparatus comprising a controller and a negative pressure source is disclosed. The negative pressure source is configured to provide negative pressure via a fluid flow path to a wound dressing, the wound dressing comprising a stabilizing structure, the stabilizing structure configured to be inserted into a wound and further configured to collapse upon application of negative pressure to the wound when the stabilizing structure is positioned in the wound. The method includes: monitoring pressure in the fluid flow path; determining a measure of collapse of the stabilizing structure from the pressure in the fluid flow path while the negative pressure source maintains a magnitude of the pressure in the fluid flow path within a negative pressure range; and outputting an indication responsive to the measure of collapse. The method is performed by the controller.

The method of the preceding paragraph can include one or more of the following features: The determining the measure of collapse comprises determining the measure of collapse from a change in the magnitude of the pressure in the fluid flow path over time. The determining the measure of collapse comprises determining the measure of collapse from a comparison of the magnitude of the pressure in the fluid flow path over time to a pressure change pattern. The pressure change pattern is indicative of one or more of: (i) pressure magnitude in the fluid flow path when the stabilizing structure is fully collapsed, (ii) pressure magnitude in the fluid flow path when the stabilizing structure is partially collapsed, or (iii) pressure magnitude in the fluid flow path when the stabilizing structure is not collapsed. The measure of collapse comprises a rate of collapse of the stabilizing structure. The outputting the indication comprises outputting the indication to (i) activate or deactivate the negative pressure source, (ii) activate or deactivate an alarm, (iii) increase or decrease a target negative pressure provided by the negative pressure source, or (iv) release negative pressure in the fluid flow path. The outputting the indication comprises outputting the indication to control activation and deactivation of the negative pressure source for a time period according to a target level of collapse of the stabilizing structure rather than to control activation and deactivation of the negative pressure source to adjust the magnitude of pressure to target a predetermined negative pressure threshold. The time period is at least 1 minutes, 5 minutes, 10 minutes, 30 minutes, 1 hour, or 5 hours. The outputting the indication comprises outputting the indication for presentation to a user or storage in a memory device. The method can further include storing, in a memory device, device usage data in association with the indication, and the device usage data comprises one or more of a pressure level, an alarm, an exudate level, an event log, and an operation use time. The method can further include determining whether the wound dressing comprises the stabilizing structure from the pressure in the fluid flow path. The monitoring the pressure in the fluid flow path comprises monitoring the pressure in the fluid flow path at the wound dressing, in one or more lumens of the fluid flow path, or at an inlet of the negative pressure source. The negative pressure source is configured to perform negative pressure therapy when a magnitude of the pressure in the fluid flow path is maintained within the negative pressure range.

In some embodiments, a wound therapy apparatus is disclosed. The wound therapy apparatus includes: a wound dressing comprising a stabilizing structure configured to be inserted into a wound; a negative pressure source configured to provide negative pressure via a fluid flow path to the wound dressing; and a controller. The controller is configured to: monitor a rate of fluid removal from the wound and wirelessly communicate the rate of fluid removal to a remote device, and output an indication when the rate of fluid removal meets a threshold.

The wound therapy apparatus of the preceding paragraph can include one or more of the following features: The controller is further configured to cause the negative pressure source to adjust a level of negative pressure provided to the wound dressing when the rate of fluid removal meets the threshold. The controller is further configured to monitor the rate of fluid removal from a weight of fluid aspirated from the wound. The controller is further configured to monitor the weight of fluid aspirated from the wound and a weight of fluid stored in a canister. The wound therapy apparatus can further include a pressure sensor configured to monitor one or more characteristics of pressure in the fluid flow path, and wherein the controller is further configured to monitor the rate of fluid removal using the one or more characteristics of pressure. The wound therapy apparatus can further include a canister configured to store fluid removed from the wound, and wherein the controller is further configured to monitor the rate of fluid removal from a level of fluid in the canister. The controller is further configured to monitor the level of fluid in the canister using one or more characteristics of pressure in the fluid flow path. The controller is further configured to monitor the level of fluid in the canister from an activity level of the negative pressure source. The negative pressure source comprises a vacuum pump, and the activity level of the negative pressure source corresponds to a speed of the vacuum pump. The one or more characteristics of pressure comprises a magnitude of pressure signals, and the magnitude of pressure signals increases as the level of fluid in the canister increases. The controller is further configured to wirelessly communicate the rate of fluid removal to the remote device to cause the remote device to store the rate of fluid removal in an electronic medical record associated with the patient.

In some embodiments, a method of operating a negative pressure wound therapy apparatus comprising a controller and a negative pressure source is disclosed. The negative pressure source is configured to provide negative pressure via a fluid flow path to a wound dressing, the wound dressing comprising a stabilizing structure inserted into a wound. The method includes: monitoring a rate of fluid removal from the wound; wirelessly communicating the rate of fluid removal to a remote device; and outputting an indication when the rate of fluid removal meets a threshold. The method is performed by the controller.

The method of the preceding paragraph can include one or more of the following features: The method further includes adjusting a level of negative pressure provided by the negative pressure source to the wound dressing when the rate of fluid removal meets the threshold. The monitoring the rate of fluid removal comprises monitoring the rate of fluid removal from a weight of fluid aspirated from the wound. The monitoring the rate of fluid removal comprises monitoring the weight of fluid aspirated from the wound and a weight of fluid absorbed by the wound dressing or stored in a canister. The method further includes monitoring one or more characteristics of pressure in the fluid flow path, and wherein the monitoring the rate of fluid removal comprises monitoring the rate of fluid removal using the one or more characteristics of pressure. The monitoring the rate of fluid removal comprises monitoring the rate of fluid removal from a level of fluid in a canister that stores fluid removed from the wound. The monitoring the rate of fluid removal comprises monitoring the level of fluid in the canister using one or more characteristics of pressure in the fluid flow path. The monitoring the rate of fluid removal comprises monitoring the level of fluid in the canister from an activity level of the negative pressure source. The negative pressure source comprises a vacuum pump, and the activity level of the negative pressure source corresponds to a speed of the vacuum pump. The one or more characteristics of pressure comprises a magnitude of pressure signals, and wherein the magnitude of pressure signals increases as the level of fluid in the canister increases. The wirelessly communicating the rate of fluid removal comprises wirelessly communicating the rate of fluid removal to the remote device to cause the remote device to store the rate of fluid removal in an electronic medical record associated with the patient.

BRIEF DESCRIPTION OF THE DRAWINGS

Features and advantages of the present disclosure will be apparent from the following detailed description, taken in conjunction with the accompanying drawings of which.

DETAILED DESCRIPTION

Introduction

Figure 1:
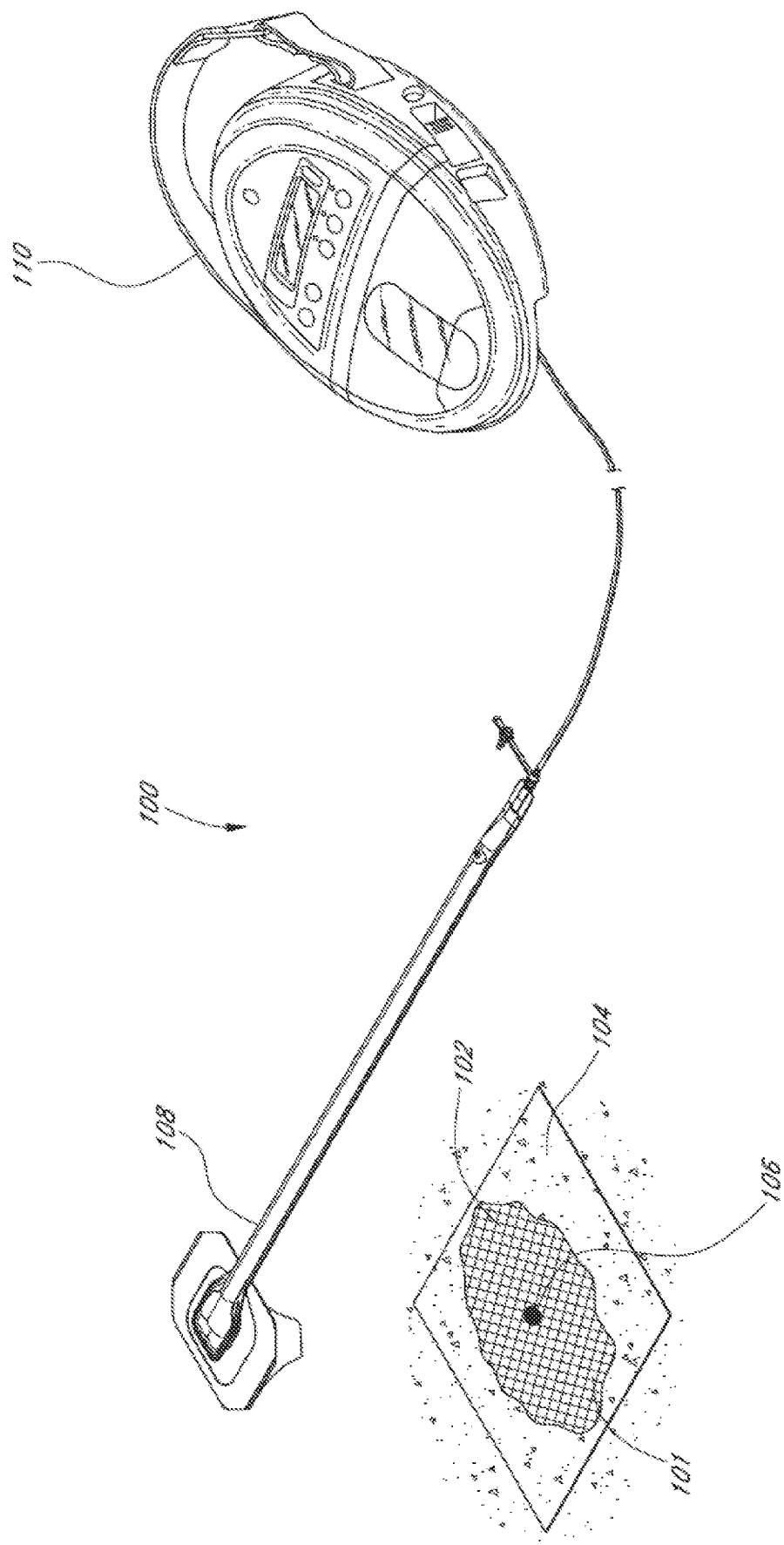
FIGS. 1, 2, and 3 illustrate embodiments of a negative pressure treatment system.

The present disclosure relates to methods and apparatuses for dressing and treating a wound with reduced pressure therapy or topical negative pressure (TNP) therapy, as well positive pressure therapy or wound care that is not aided by applied pressure. In particular, but without limitation, embodiments of this disclosure relate to negative pressure therapy apparatuses, methods for controlling the operation of TNP systems, and methods of using TNP systems. The methods and apparatuses can incorporate or implement any combination of the features described below.

The apparatuses and components including the wound overlay and packing materials, if any, are sometimes collectively referred to herein as wound dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, electrical burns, diabetic ulcers, pressure ulcers, stoma, surgical wounds, trauma and venous ulcers or the like.

As is used in this section or elsewhere in this specification, reduced or negative pressure levels, such as –X mmHg, represent pressure levels that are below atmospheric pressure, which typically corresponds to 760 mmHg (or 1 atm, 29.93 inHg, 101.325 kPa, 14.696 psi, etc.). Accordingly, a negative pressure value of –X mmHg reflects pressure that is X mmHg below atmospheric pressure, such as a pressure of (760-X) mmHg. In addition, negative pressure that is "less" or "smaller" than –X mmHg corresponds to pressure that is closer to atmospheric pressure (e.g., –40 mmHg is less than –60 mmHg). Negative pressure that is "more" or "greater" than –X mmHg corresponds to pressure that is further from atmospheric pressure (e.g., –80 mmHg is more than –60 mmHg).

Although one or more features described herein may be discussed in the context of negative pressure wound therapy, the one or more features can apply to other contexts like positive pressure wound therapy or traditional wound therapy without application of pressure.

Overview

During treatment of a patient's wound using a TNP apparatus, the TNP apparatus may remove fluids including wound exudate from the wound. To help ensure that fluid removal from the wound remains within acceptable performance limits for the TNP apparatus and acceptable health or comfort limits for the patient, the TNP apparatus can include a controller that automatically monitors and tracks a volume or rate of fluid removal from the wound, such as a total volume of fluid removal, an instantaneous rate of fluid removal, or a rate of fluid removal per time period (such as over a last five or last one hour). The controller can use one or more sensors to monitor the volume or rate of fluid removal, communicate data to another device, control operation of the TNP apparatus, or provide an indication to a user of the TNP apparatus responsive to the volume or rate of fluid removal.

The one or more sensors used by the controller to monitor the volume or rate of fluid removal can, for example, include a scale, a level sensor, a pressure sensor, or an activity sensor. The scale can measure a weight of fluid removed from the wound, for instance, by weighing a canister or a wound dressing (which can also be or include any of the wound closure devices described herein) that collects and stores fluid removal from the wound. Because the weight of removed fluid can be generally proportional to the volume of fluid removal, the controller can use the weight to monitor the volume or rate of fluid removal. The fluid level sensor can measure a level of fluid in a canister (or wound dressing) which collects and stores fluid removed from the wound. The level of fluid in the canister (or wound dressing) can be generally proportional to the volume of removed fluid and thus can be used by the controller to monitor the volume or rate of fluid removal. The pressure sensor can measure pressure in a fluid flow path through which the TNP apparatus provides negative pressure to the wound. The controller, in such implementations, can analyze one or more characteristics of pressure in the fluid flow path, such as magnitude of pressure pulses, to determine and monitor the volume or rate of fluid removal. The activity sensor can measure a level of activity of the TNP apparatus, such as a speed of a negative pressure source actuator (such as a motor) of the TNP apparatus, and the controller can use the level of activity to determine and monitor the volume or rate of fluid removal.

The controller can store in a memory device one or more values indicative of the volume or rate of fluid removal over time for additional processing. In one example, the controller may then manually in response to user input or automatically transmit the one or more values using a transmitter of the TNP apparatus to a remote device. The controller can, for instance, transmit via a wireless communication network the one or more values in a message that upon receipt by the remote device causes the remote device to store the one or more values in an electronic medical record associated with a user of the TNP apparatus or an individual prescribed to use the TNP apparatus. In another example, the controller can provide a notification (such as output an alarm) when the volume or rate of fluid removal meets a threshold that indicates an excess fluid removal or sudden increase or decrease in fluid removal. In yet another example, the controller can automatically increase or decrease one or more operational parameters, such as negative pressure provided by the TNP apparatus to the wound, according to the volume or rate of fluid removal.

The controller can moreover utilize information about a patient, such as patient metabolism or physiology or data from other treatment of the patient, in combination with the volume or rate of fluid removal to communicate data to another device, control operation of the TNP apparatus, or provide an indication to a user of the TNP apparatus. In one example, the controller can receive information about a volume or rate of fluid that may be provided to the patient (which may include intravenous fluids, drugs, or painkillers) and use the volume or rate of fluid provided to the patient to adjust a threshold used to trigger activity by the TNP apparatus. It may be particularly important to ensure during the first few days of treating a wound that more fluids are going into a patient than are removed from the wound. Thus, the controller can, for instance, compare the volume of fluid provided to the patient with the volume of fluid removal from the wound and provide a notification (such as trigger an alarm) if the volume of fluid removal meets or exceeds the volume of fluid provided to the patient. The controller can additionally or alternatively automatically adjust one or more operational parameters, such as the level of negative pressure provided by the TNP apparatus, to attempt to decrease the rate of fluid removal from the wound. In another example, the controller can receive information about the metabolism or physiology of the patient and adjust a threshold used to trigger activity by the TNP apparatus responsive to the volume or rate of fluid removal. The controller, as a result, can be more sensitive to the volume or rate of fluid removal for certain individual than other individuals (such as more sensitive to the volume or rate of fluid removal in smaller individuals than larger individuals) or at certain times than other times (such as when a patient is in critical condition rather than in stable condition).

A wound dressing used in negative wound pressure therapy can include a wound matrix or a stabilizing structure configured to collapse when negative pressure is applied to a wound in which the stabilizing structure is placed or positioned, as well as when a wound closes and heals. The stabilizing structure can be rigid or substantially rigid. The collapse of the stabilizing structure, however, can be difficult to monitor once the stabilizing structure is placed in the wound because the stabilizing structure may be difficult to see within the wound or through a drape, foam, or another wound dressing component placed over the stabilizing structure.

A TNP apparatus can include a controller that monitors pressure in a fluid flow path connecting a source of negative pressure to a wound dressing including a stabilizing structure. The controller can advantageously, in certain embodiments, monitor a state of collapse of the stabilizing structure based on the pressure in the fluid flow path. The stabilizing structure can change negative pressure wound therapy dynamics, such as during a continuous or an intermittent operation mode of the TNP apparatus, and the state of collapse of the stabilizing structure can cause pressure changes, noise, or artifacts, such as due to a non-homogeneous compression or decompression of the stabilizing structure. Such pressure artifacts may be detected and analyzed to determine the state of collapse of the stabilizing structure. For example, unlike foam which may become substantially flat when sufficient negative pressure is applied (such as, −80 mmHg) and may not collapse further even when negative pressure is increased, the stabilizing structure may collapse over a larger range of negative pressures. Collapse of the stabilizing structure can cause variations in the pressure levels, such as pressure artifacts. This may be due to the removal of air from the cells of the stabilizing structure, which causes its collapse.

The controller can, for example, determine a measure of collapse of the stabilizing structure from the pressure changes in the fluid flow path and output an indication responsive to the measure of collapse. The pressure changes can be detected using one or more pressure sensors in the fluid flow path. The measure of collapse can be determined, for instance, using one or more of a peak-to-peak magnitude of pressure variation, a statistical pressure algorithm, a pressure pattern matching, pressure micro-changes like in envelope changes in pressure signal, or pressure frequency variation, among other approaches. The measure of collapse can, in some instances, be a degree or rate of collapse of the stabilizing structure and indicative of a degree or rate of closure of the wound.

The controller can monitor the healing of the wound from the measure of collapse as the wound closes and heals. The healing or closing of the wound can cause the collapse of the stabilizing structure beyond what may be expected when a particular level of negative pressure is applied to the wound incorporating the stabilizing structure. As a result, the controller can determine that a degree or rate of collapse in excess of the degree or rate of collapse attributable to application of negative pressure may be attributable to wound healing or closure. In such implementations, the indication output by the controller can be output for presentation to user and denote to replace the stabilizing structure with a smaller stabilizing structure that may be more appropriate for the wound since the wound has partially healed or closed.

The controller can control provision of wound therapy, a degree or rate of collapse of the stabilizing structure, a size of the wound, an amount or rate of fluid removed from the wound, or an amount or rate of pain experienced based on the measure of collapse. For example, the controller can, at least for a period of time (like 30 seconds, 1 minutes, 2 minutes, 3 minutes, 5 minutes, or 10 minutes) or for a number of compression or decompression cycles (like 2, 3, 5, 10, 20, or 50, compression-decompression cycles) activate or deactivate a negative pressure source according to the measure of collapse. Moreover, the controller can activate or deactivate the negative pressure source according to the measure of collapse in addition to or instead of controlling the negative pressure source to target a specific level or a range of negative pressure. Such control advantageously can, in certain embodiments, enable provision of therapy to be tailored to a particular wound, environment or patient (such as in a non-linear way), which thereby can enable faster, less painful, more effective, or more responsive therapy. In addition, such control may enable the controller to be more reactive to or prevent blockages in the fluid flow path because more tailored or customized negative pressure therapy can be applied based on, for example, measured fluid removal from the wound. For example, more appropriate level (or levels) of negative pressure can be continuously selected based on the measured fluid removal, which can result in a lessened risk of a blockage as negative pressure being applied in tailored to the rate of flow of removed fluid.

The controller can determine, prior to initiating or reinitiating provision of therapy, one or more characteristics of a wound dressing from the pressure in the fluid flow path. The one or more characteristics can include a size of the wound dressing, a type of the wound dressing, or whether the wound dressing includes a stabilizing structure. In one example, in response to determining that the wound dressing includes the stabilizing structure, the controller can determine to control application of negative pressure based on the measure of collapse, and in response to determining that the wound dressing does not include the stabilizing structure, the controller can determine to control application of negative pressure instead to a pressure setpoint.

The controller can detect or characterize patient movement from pressure variations in the fluid flow path due to shifts in the stabilizing structure of a wound dressing. The patient movement can include, for instance, leg or arm movement or breathing by the patient (for example, when the stabilizing structure is placed in an abdominal wound).

The controller can determine whether a suture burst or failed from pressure variations in the fluid flow path. The suture may be used to hold together tissue near a wound dressing. In one example, the controller may monitor cycles of variations in pressure, such as in a peak-to-peak pressure signal, and detect a spike in pressure that may be indicative of a volume change of the wound due to a burst or failed suture.

Pressure Therapy Systems

FIG. 1 illustrates an embodiment of a negative pressure treatment system 100 that comprises a wound packer 102 inserted into a wound 101. The wound packer 102 may comprise porous materials such as foam, and in some embodiments may comprise one or more embodiments of wound closure devices described in further detail in this section or elsewhere in this specification. In some embodiments, the perimeter or top of any wound closure device inserted into the wound 101 may also be covered with foam or other porous materials. A single drape 104 or multiple drapes may be placed over the wound 101, and is preferably adhered or sealed to the skin on the periphery of the wound 101 so as to create a fluid-tight seal. An aperture 106 may be made through the drape 104 which can be manually made or preformed into the drape 104 so as to provide a fluidic connection from the wound 101 to a source of negative pressure such as a TNP apparatus 110 that includes a pump. Preferably, the fluidic connection between the aperture 106 and the pump of the TNP apparatus 110 is made via a conduit 108. In some embodiments, the conduit 108 may comprise a RENASYS® Soft Port™, manufactured by Smith & Nephew. Of course, in some embodiments, the drape 104 may not necessarily comprise an aperture 106, and the fluidic connection to the pump of the TNP apparatus 110 may be made by placing the conduit 108 below the drape. In some wounds, particularly larger wounds, multiple conduits 108 may be used, fluidically connected via one or more apertures 106.

In some embodiments, the drape 104 may be provided with one or more corrugations or folds. Preferably, the corrugations are aligned along the longitudinal axis of the wound, and as such may support closure of the wound by preferentially collapsing in a direction perpendicular to the longitudinal axis of the wound. Such corrugations may aid in the application of contractile forces parallel to the wound surface and in the direction of wound closure. Examples of such drapes may be found in application Ser. No. 12/922,118, titled "Vacuum Closure Device," filed Nov. 17, 2010 (published as US 2011/0054365), which is hereby incorporated by reference in its entirety.

In use, the wound 101 is prepared and cleaned. In some cases, such as abdominal wounds, a non- or minimally-adherent organ protection layer (not illustrated) may be applied over any exposed viscera. The wound packer 102 is then inserted into the wound, and is covered with the drape 104 so as to form a fluid-tight seal. A first end of the conduit 108 is then placed in fluidic communication with the wound, for example via the aperture 106. The second end of the conduit 108 is connected to the TNP apparatus 110. The pump of the TNP apparatus 110 may then be activated so as to supply negative pressure to the wound 101 and evacuate wound exudate from the wound 101. As will be described in additional detail below and in relation to the embodiments of the foregoing wound closure devices, negative pressure may also aid in promoting closure of the wound 101, for example by approximating opposing wound margins.

Any structure or component disclosed herein this section or elsewhere in the specification may comprise a radiopaque material. A radiopaque material advantageously allows a clinician to more easily find pieces of the wound closure device that may have come loose from the structure and become lost in the wound. Some examples of radiopaque materials include barium sulfate, bismuth trioxide, bismuth subcarbonate, bismuth oxychloride, and tungsten.

Figure 2:
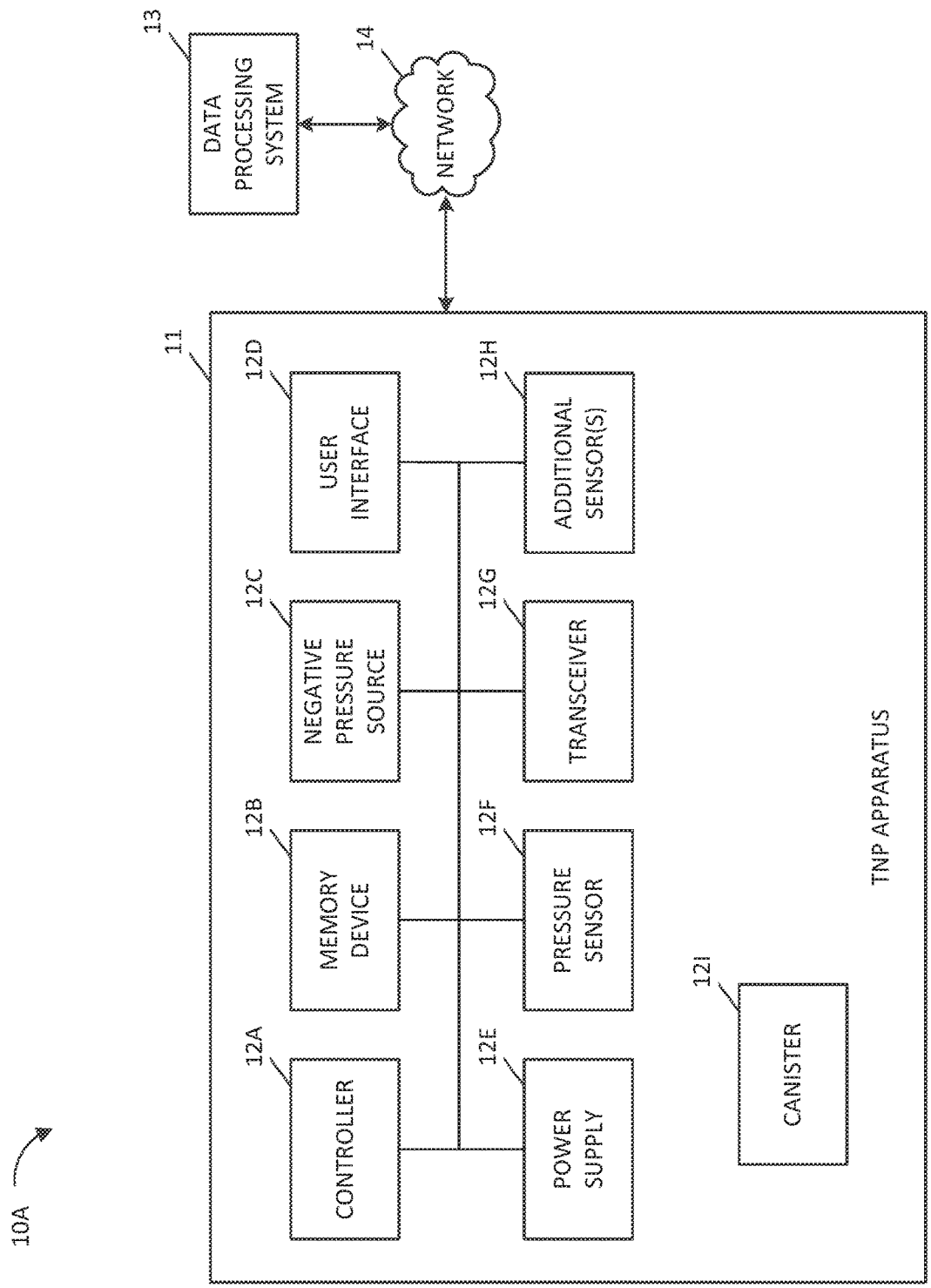

FIG. 2 illustrates a negative pressure therapy system 10A according to some embodiments. The system 10A includes a TNP apparatus 11 (which may be similar to the TNP apparatus 110 and the TNP apparatus of the Overview section) and a remote data processing system 13. The TNP apparatus 11 can be used to treat a wound using a wound dressing that is in fluidic communication with the TNP apparatus 11 via a fluid flow path. The TNP apparatus 11 can include a controller 12A (which may be similar to the controller of the Overview section), a memory device 12B, a negative pressure source 12C, a user interface 12D, a power supply 12E, a pressure sensor 12F, a transceiver 12G, and additional sensor(s) 12H that are configured to electrically communicate with one another. The TNP apparatus 11 can include a canister 12I that collects fluid including wound exudate. In some embodiments, wound exudate can additionally or alternatively be absorbed by a wound dressing and the canister 12I then may or may not be used.

The controller 12A can control operations of one or more other components of the TNP apparatus 11 according at least to instructions stored in the memory device 12B. The controller 12A can, for instance, control operations of and supply of negative pressure by the negative pressure source 12C. The negative pressure source 12C can include a pump, such as, without limitation, a rotary diaphragm pump or other diaphragm pump, a piezoelectric pump, a peristaltic pump, a piston pump, a rotary vane pump, a liquid ring pump, a scroll pump, a diaphragm pump operated by a piezoelectric transducer, a voice coil pump, or any other suitable pump or micropump or any combinations of the foregoing. The user interface 12D can include one or more elements that receive user inputs or provide user outputs to a patient or caregiver. The one or more elements that receive user inputs can include buttons, switches, dials, touch screens, microphones, or the like. The one or more elements that provide user outputs can include lights, displays, speakers, or the like.

Figure 3:
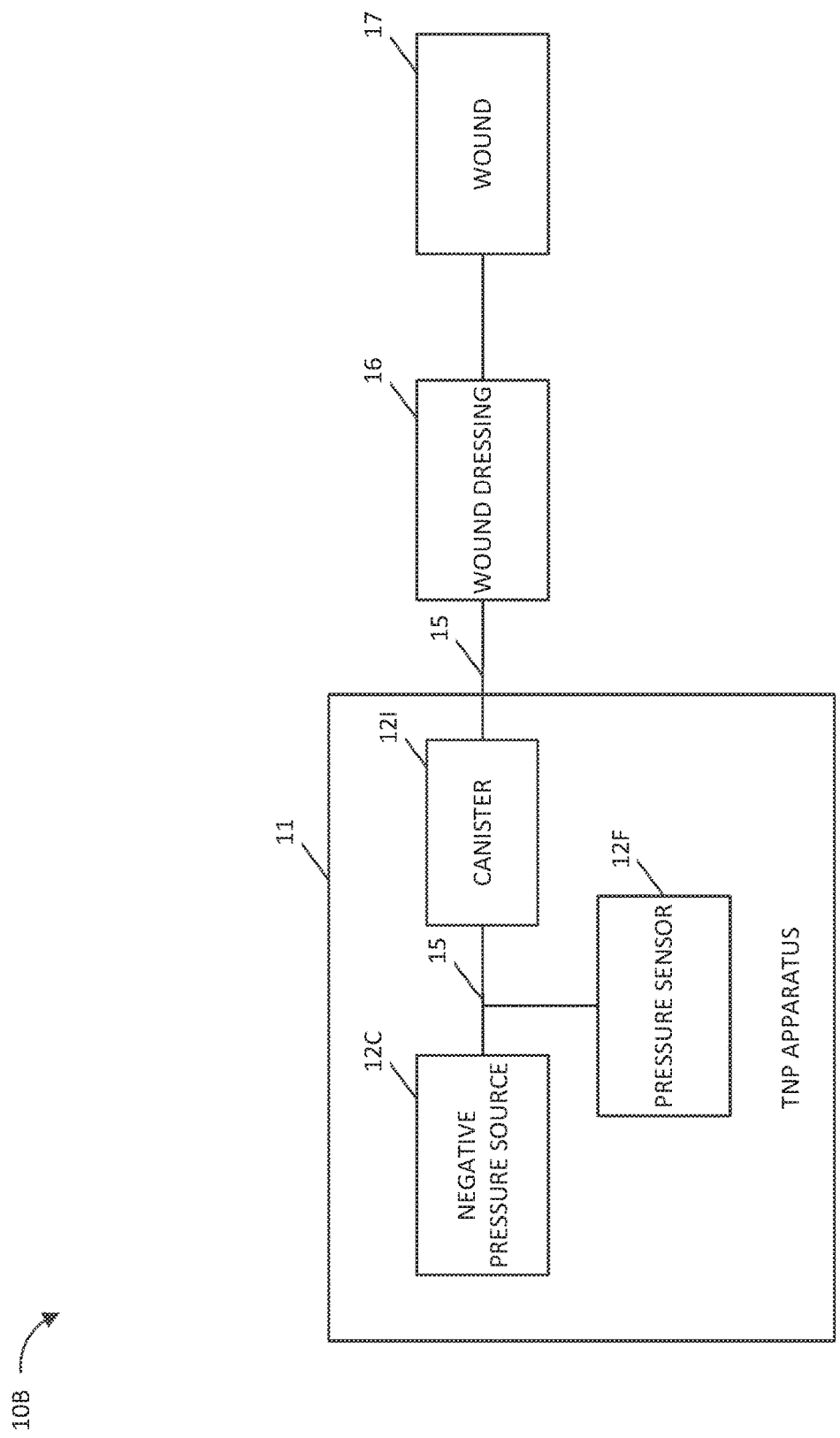

The pressure sensor 12F can be used to monitor pressure underneath a wound dressing, such as by monitoring (i) pressure in a fluid flow path connecting the negative pressure source 12C and the wound dressing as illustrated by FIG. 3, (ii) pressure at or in the wound dressing, or (iii) pressure at or in the negative pressure source 12C. In some implementations, the pressure sensor 12F can include at least two pressure sensors that are positioned in or fluidically connected to the fluid flow path to permit differential measurement of the pressure, such as differential measurement between pressure at or near the wound and pressure at or near the TNP apparatus 11. For example, a first pressure sensor can be positioned upstream of the wound (such as at or near the inlet of the negative pressure source 12C) and a second pressure sensor can be positioned to detect pressure at or near the wound or at or near a canister. This configuration can be accomplished by incorporating, in addition to one or more lumens forming a first fluid flow path connecting the negative pressure source 12C to the wound, a second fluid flow path that includes one or more lumens connecting the TNP apparatus 11 to the wound and through which the second pressure sensor can monitor pressure at or near the wound or at or near a canister. The first and second fluid flow paths can be fluidically isolated from each other.

FIG. 3 illustrates a negative pressure therapy system 10B according to some embodiments. The system 10B includes the TNP apparatus 11, as well as a fluid flow path 15, a wound dressing 16, and a wound 17. The TNP apparatus 11 can be used to treat the wound 17 using the wound dressing 16 that is in fluidic communication with the negative pressure source 12C via the fluid flow path 15. The pressure sensor 12F is depicted in FIG. 3 as being positioned in the fluid flow path 15, such as at or near an inlet of the TNP apparatus 11, to measure pressure in the fluid flow path 15. The wound dressing 16 can embody any of the wound dressings or wound closure devices described herein. In some implementations, the canister 12I may not be used and, instead, wound exudate can be collected by wound dressing 16 which can be absorbent. In other implementations, both the canister 121 and the wound dressing 16 can be used, and the wound dressing 16 can be absorbent.

Turning again to FIG. 2, the transceiver 12G can be used to communicate with the data processing system 13 via a network 14. The transceiver 12G can, for example, transmit device usage data like alarms, rate of fluid removal, measured pressure, or changes to a therapy program administered by the TNP apparatus 11 to the data processing system 13. The network 14 can be a communication network, such as a wireless communication network like a cellular communication network or a wired communication network. The memory device 12B can be used to store the device usage data that may then be transmitted by the transceiver 12G. The data processing system 13 can, in some implementations, automatically store data received from the transceiver 12G to an electronic medical file associated with a patient that used or is prescribed to use the TNP apparatus 11. The transceiver 12G can, in some instances, include a transmitter to transmit data separate from a receiver used to receive data.

The additional sensor(s) 12H can include, for example, a level senor that detects a level of fluid in the canister 121 or a scale that weighs one or more components of the negative pressure therapy systems 10A and 10B like the canister 121 or the wound dressing 16. The controller 12A can use the additional sensor(s) 12H to monitor a rate of fluid removal from a wound, such as the wound 17.

Stabilizing Structures and Wound Closure Devices

Figure 4A:
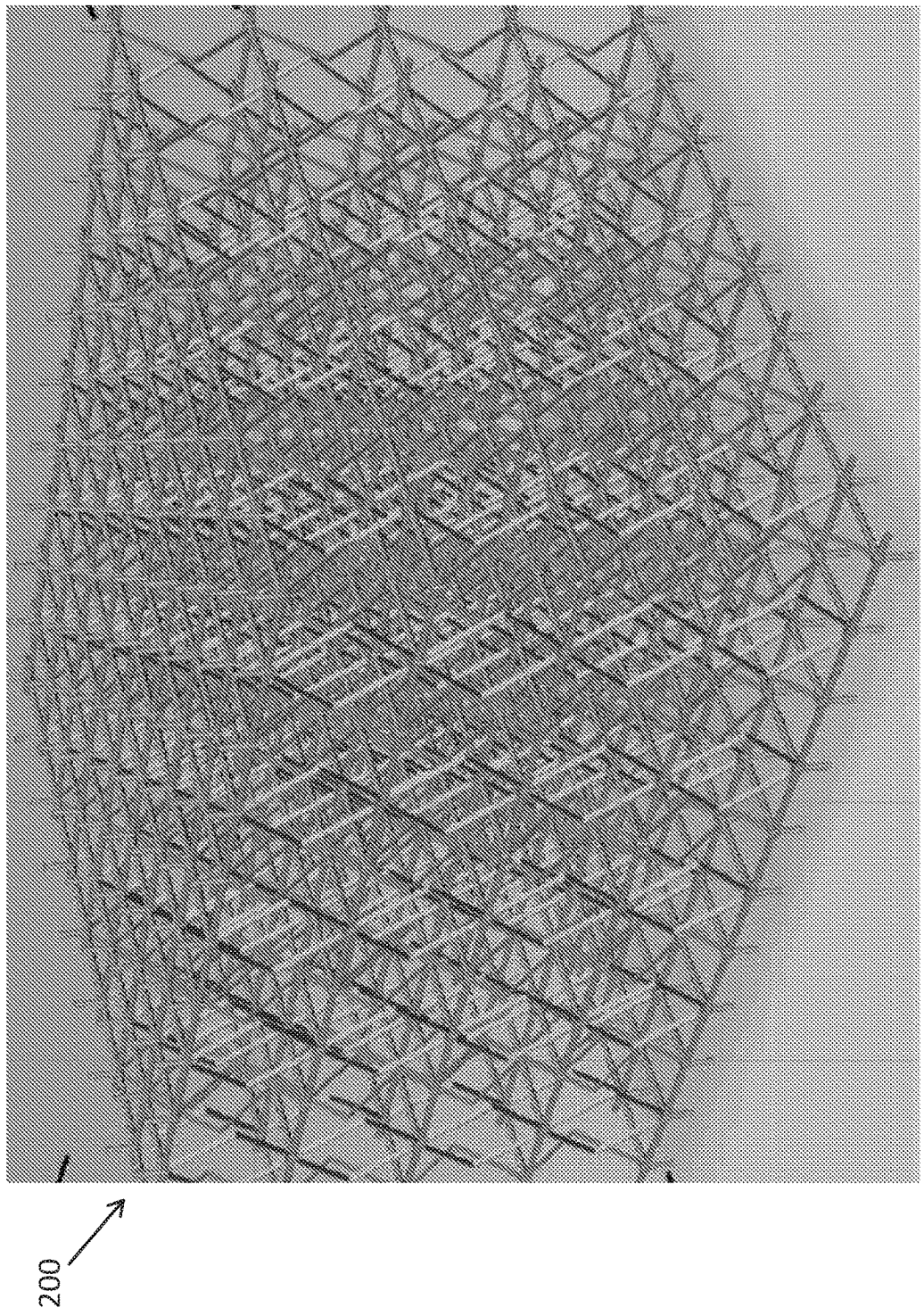
FIGS. 4A, 4B, and 4C illustrate multiple views of embodiments of a stabilizing structure.
Figure 4B:
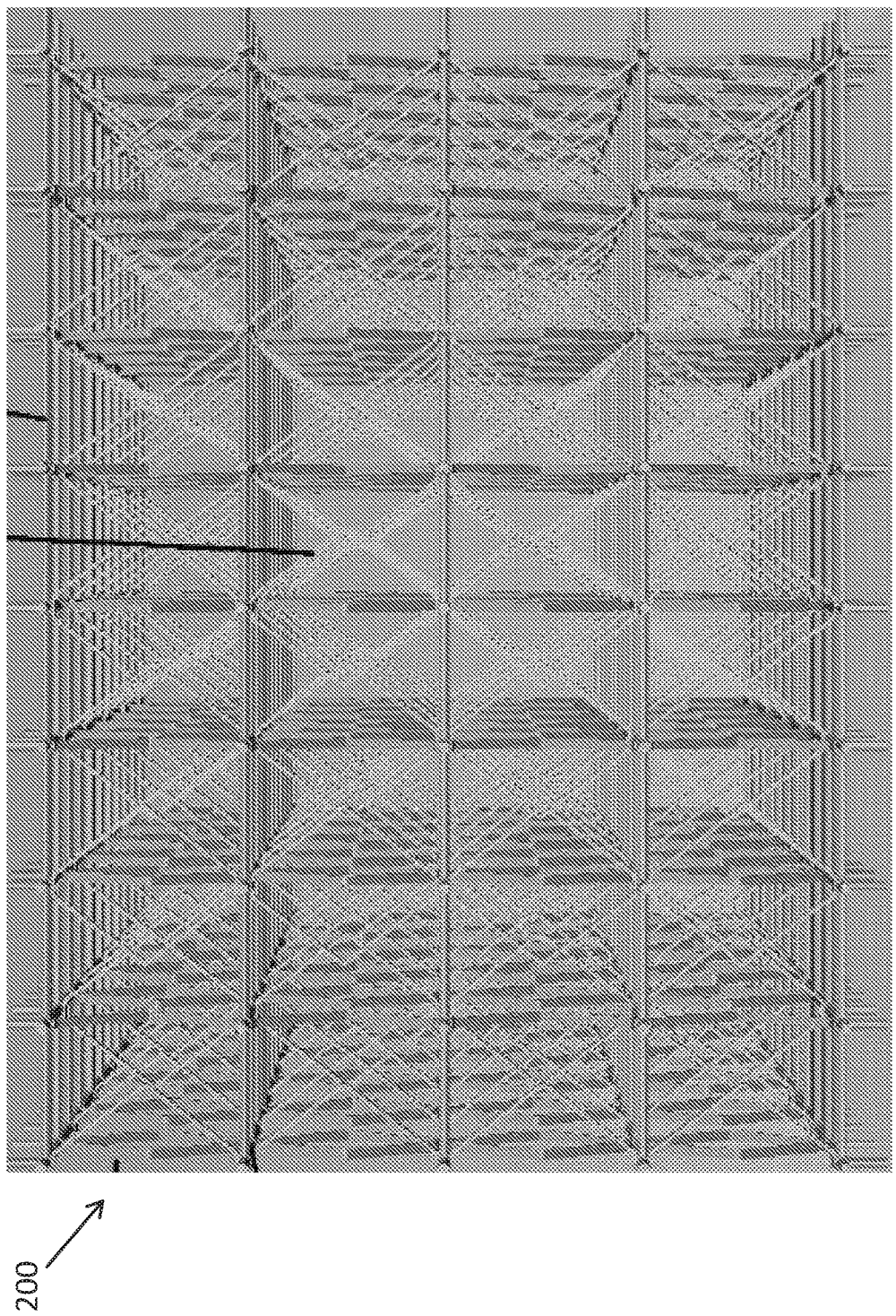
Figure 4C:
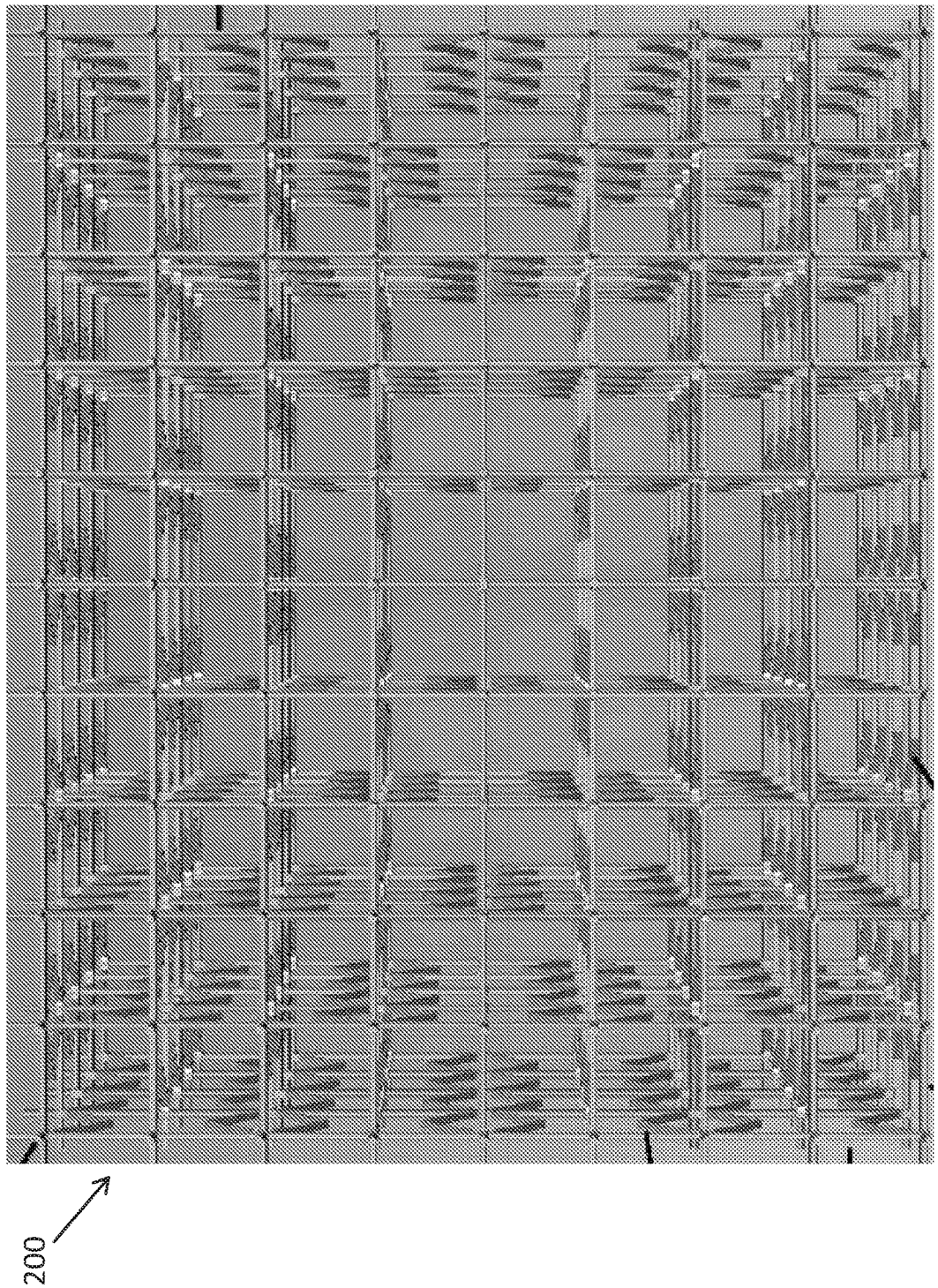

FIGS. 4A, 4B, and 4C illustrate multiple views of embodiments of a stabilizing structure 200. The stabilizing structure 200 can collapse in any manner described in this section or elsewhere in this specification with or without the application of negative pressure. For example, the stabilizing structure may collapse significantly more in one plane than in another plane upon application of negative pressure. In some embodiments, the stabilizing structure is configured to collapse more in a horizontal plane parallel to the length and width of the stabilizing structure than in a vertical plane perpendicular to the horizontal plane. In embodiments, particular rows may collapse in a first direction, while another row may collapse in the same or an opposing direction. In certain embodiments, the stabilizing structure may collapse along the width of the stabilizing structure while remaining relatively rigid along the length of the stabilizing structure and in the vertical direction.

The stabilizing structure may be comprised of any materials described in this section or elsewhere in this specification, including: flexible plastics such as silicone, polyurethane, rigid plastics such as polyvinyl chloride, semi-rigid plastics, semi-flexible plastics, biocompatible materials, composite materials, metals, and foam. In certain embodiments, the stabilizing structure may comprise a radio opaque material, to more readily allow a clinician to find pieces of the stabilizing structure within the wound.

Further details regarding the wound closure devices, stabilizing structures, related apparatuses and methods of use that may be combined with or incorporated into any of the embodiments described herein are found elsewhere throughout this specification and in International Application No. PCT/US2013/050698, filed Jul. 16, 2013, published as WO 2014/014922 A1, the entirety of which is hereby incorporated by reference.

Pressure Therapy Methods

Figure 5:
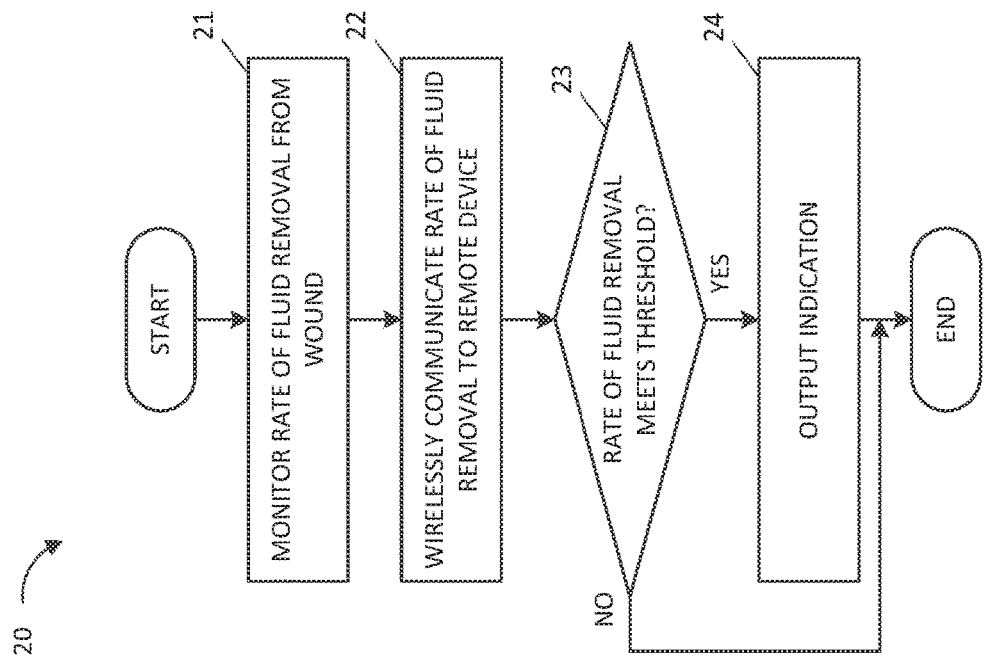
FIG. 5 illustrates a fluid removal management process according to some embodiments.

FIG. 5 illustrates a fluid removal management process 20 performable by a device, such as the controller 12A of the TNP apparatus 11 or a controller of the TNP apparatus 110. For convenience, the fluid removal management process 20 is described in the context of the TNP apparatus 11 of FIGS. 2 and 3, but may instead be implemented in other systems described herein or by other computing systems not shown. The fluid removal management process 20 can advantageously, in certain embodiments, enable the TNP apparatus 11 to monitor a rate of fluid removal from the wound 17 and automatically wirelessly communicate the rate of fluid removal to another device and output an indication when the rate of fluid removal becomes excessive.

At block 21, the fluid removal management process 20 can monitor a rate of fluid removal from the wound 17. For example, the fluid removal management process 20 can use measurements provided by one or more sensors, like the pressure sensor 12F or the additional sensor(s) 12H, to monitor the rate of fluid removal.

At block 22, the fluid removal management process 20 can wirelessly communicate the rate of fluid removal to the data processing system 13. The fluid removal management process 20 can, for instance, use the transceiver 12G to communicate the rate of fluid removal via the network 14 to the data processing system 13. The fluid removal management process 20 can communicate over a wired interface rather than or in addition to wirelessly in some implementations.

At block 23, the fluid removal management process 20 can determine whether the rate of fluid removal meets a threshold. The thresholds can be a rate threshold whose magnitude indicates an excessive fluid rate increase or decrease during delivery of negative pressure therapy with the TNP apparatus 11.

When the rate of fluid removal meets the threshold, at block 24, the fluid removal management process 20 can output an indication that the rate of fluid removal experienced an excessive fluid rate increase or decrease during delivery of negative pressure therapy with the TNP apparatus 11. The indication can, for instance, include activation a visible or audible alarm of the user interface 12D or display of a textual warming message on a display of the user interface 12D.

On the other hand, when the rate of fluid removal does not meet the threshold, the fluid removal management process 20 can end.

Figure 6:
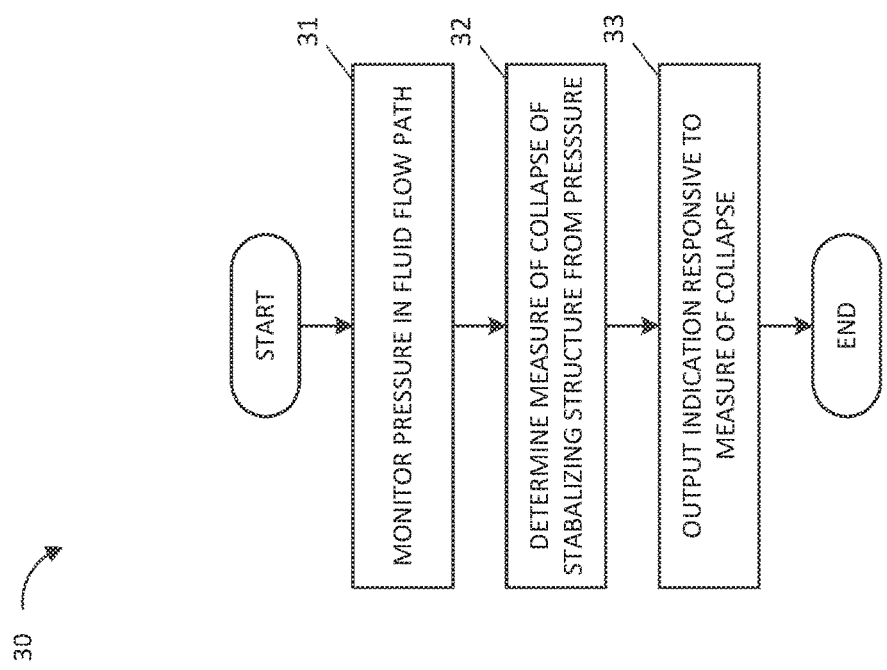
FIG. 6 illustrates a collapse monitoring process according to some embodiments.

FIG. 6 illustrates a collapse monitoring process 30 performable by a device, such as the controller 12A of the TNP apparatus 11 or a controller of the TNP apparatus 110. For convenience, the collapse monitoring process 30 is described in the context of the TNP apparatus 11 of FIGS. 2 and 3, but may instead be implemented in other systems described herein or by other computing systems not shown. The collapse monitoring process 30 can advantageously, in certain embodiments, enable the TNP apparatus 11 to monitor collapse of a stabilizing structure of the wound dressing 16 placed in the wound 17 from pressure in the fluid flow path 15 and appropriately control operation of the TNP apparatus 11.

At block 31, the collapse monitoring process 30 can monitor pressure in a fluid flow path. For example, the controller 12A can monitor pressure using the pressure sensor 12F or the additional sensor(s) 12H positioned to detect the pressure in the fluid flow path 15.

At block 32, the collapse monitoring process 30 can determine a measure of collapse of a stabilizing structure of a wound dressing. For example, the controller 12A can determine a measure of collapse of a stabilizing structure of the wound dressing 16 from the pressure in the fluid flow path 15 detected by the pressure sensor 12F or the additional sensor(s) 12H. The measure of collapse can, for instance, be determined from a change in a magnitude or a frequency of the pressure in the fluid flow path over time as described herein. In one example, the controller can compare the magnitude over time to one or more pressure patterns indicative of one of (i) pressure magnitude in the fluid flow path when the stabilizing structure is fully collapsed, (ii) pressure magnitude in the fluid flow path when the stabilizing structure is partially collapsed, and (iii) pressure magnitude in the fluid flow path when the stabilizing structure is not collapsed, and the controller can determine the measure of collapse from a degree of similarity of the magnitude over time to the one or more of the pressure patterns. In another example, the measure of collapse can be or be related to a degree or a rate of collapse of the stabilizing structure.

At block 33, the collapse monitoring process 30 can output an indication responsive to the measure of collapse. For example, the controller 12A can output an indication according to the measure of collapse. The collapse monitoring process 30 can, in some implementations, output the indication to control activation and deactivation of the negative pressure source for a time period (such as for 1 minutes, 5 minutes, 10 minutes, 30 minutes, 1 hour, or 5 hours) according to the measure of collapse rather than to control activation and deactivation of the negative pressure source to adjust the magnitude of pressure to target a predetermined negative pressure threshold. In some implementations, the controller can output the indication for presentation to a user (such as via a visible, audible, or tactile alarm of the user interface 12D or display of a textual warming message on a display of the user interface 12D) or for storage in a memory device, such as for storage in association with device usage data like a pressure level, an alarm, an exudate level, an event log, and an operation use time. In some embodiments, at block 33, the collapse monitoring process 30 can adjust one or more parameters of negative pressure therapy, such as the negative pressure level, mode (for example, continuous or intermittent), etc. Control of negative pressure therapy can be tied to achieving or maintaining a target level of collapse of the stabilizing structure (for example, 10% when the treatment has begun, 30% after treatment has been applied for some time, etc.). Additionally or alternatively, the collapse monitoring process 30 can activate or deactivate the negative pressure source, increase or decrease a target negative pressure provided by the negative pressure source, or release negative pressure in the fluid flow path.

Fluid Detection

Figure 7:
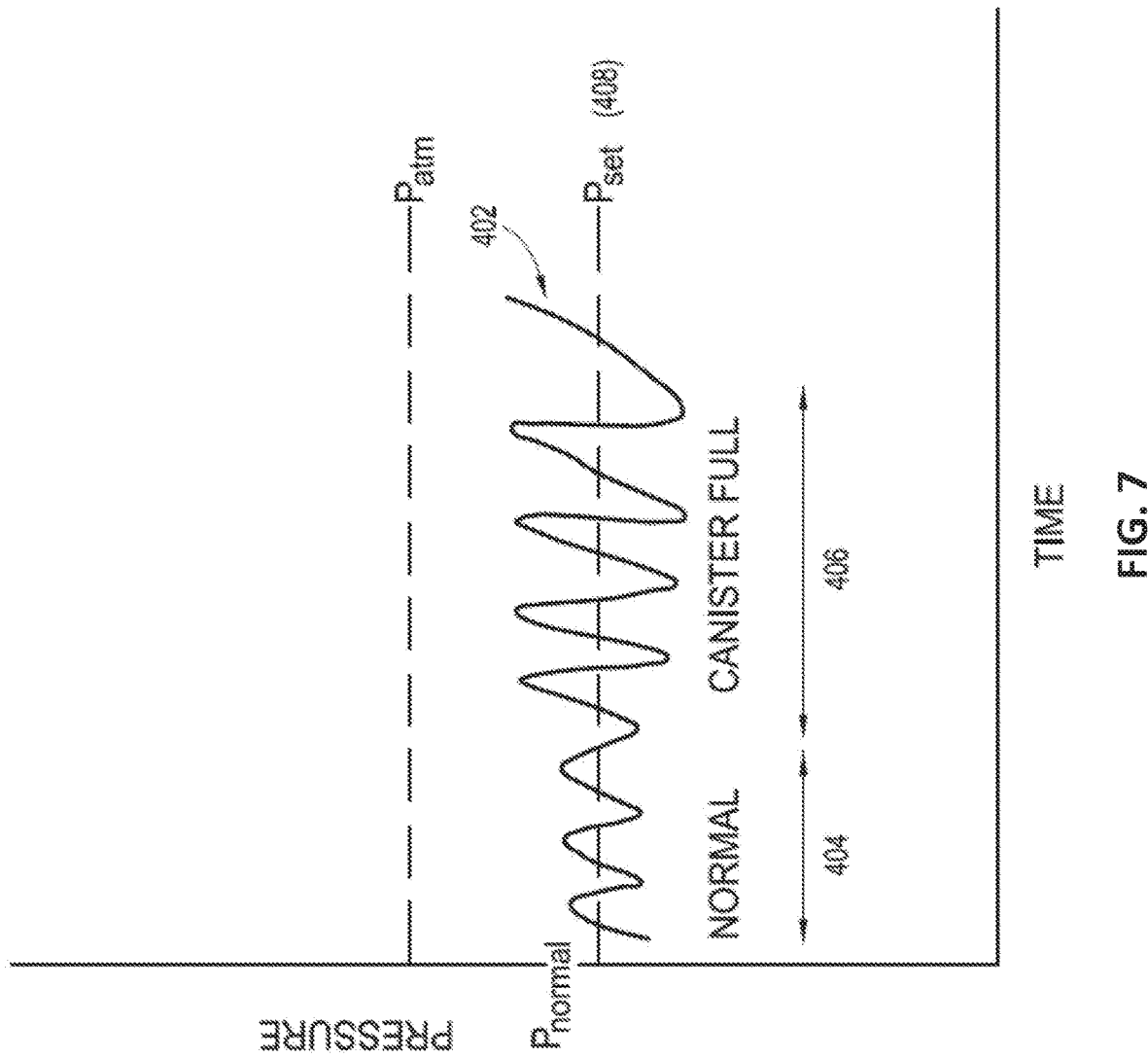
FIG. 7 illustrates a graph of pressure signals according to some embodiments.

Presence of exudate in the fluid flow path can be detected by processing data from one or more pressure sensors, such as the pressure sensor 12F. This detection can be enhanced by changing one or more settings of the negative pressure source, such as increasing the delivered vacuum level, decreasing the vacuum level, pausing or stopping the negative pressure source, changing the speed of an actuator (such as a pump motor), changing a cadence of the actuator, and the like. In some embodiments, as the negative pressure source operates, it generates pressure pulses or signals that are propagated through the fluid flow path. The pressure signals are illustrated in the pressure curve 402 of FIG. 7 according to some embodiments. As is illustrated in region 404, pressure in the fluid flow path varies or oscillates around a particular pressure setting or set point 408 (for example, as selected by the user) during normal operation of the system. Region 406 illustrates pressure pulses in the flow path when there is a blockage distal to the negative pressure source, such as the canister (or dressing) becomes full or a canister filter is occluded or blocked. As is illustrated, a distal blockage causes a reduced volume to be seen upstream of the canister (or dressing), and the amplitude of the pressure pulses increases. The frequency of a pressure signal is slowed or decreased in some embodiments. In certain embodiments, this change or "bounce" in the magnitude (or frequency) of the pressure pulse signal can be magnified or enhanced by varying the speed of the actuator, varying the cadence of the actuator, such as by adjusting pulse-width modulation (PWM) control parameters, and the like. Such adjustments of negative pressure source operation are not required but can be performed over short time duration and the changes can be small such that the operation of the system remains relatively unaffected. In some embodiments, the canister filter can be hydrophobic so that the flow of liquid is substantially blocked while the flow of air is allowed. Additional details of flow rate detection are described in U.S. Pat. No. 8,843,327, which is incorporated by reference in its entirety.

Canisterless systems can use an absorbent dressing for exudate removed from the wound. Such dressing may include absorbing or superabsorbing material to collect or retain exudate so that it is not aspirated into the negative pressure source. Similar to a canister filter, a dressing filter (which may be hydrophobic) may be used to prevent the exudate from reaching the negative pressure source. In such systems, detection of a dressing full condition or dressing filter (which may be) occluded condition can be an equivalent to detection of a canister full condition.

Changes in characteristics of pressure signals can be used to determine rate of fluid removal, distal blockages, level of exudate in the canister (or dressing), canister (or dressing) full conditions, and the like. The characteristics can include signal magnitude, frequency, shape (e.g., envelope), etc. In some embodiments, the system can detect the rate of fluid removal by monitoring the change in the magnitude of pressure pulses over time. For example, as the canister (or dressing) becomes filled with wound exudate, the magnitude of pressure pulses can increase, as illustrated in region 406. Additional details of monitoring the rate of fluid removal are disclosed in U.S. Patent Publication No. 2016/0184496, which is incorporated by reference in its entirety.

Wound Closure and Treatment Methods

The stabilizing structures or wound closure devices described in this section or elsewhere in this specification may be used in conjunction with methods or systems for the closure of a wound. In some embodiments of methods of use for closure of a wound, one or more of the stabilizing structures or wound closure devices of any of the embodiments described in this section or elsewhere in this specification is placed into a wound. In some embodiments, an organ protection layer may be provided in the wound before placement of the stabilizing structure. In certain embodiments, foam or other porous material may be placed in the wound along with the stabilizing structure or wound closure device, either below, above, or surrounding the stabilizing structure or wound closure device. Foam or other porous material may also surround the perimeter of the stabilizing structure or wound closure device.

The stabilizing structure or wound closure device may be configured to collapse in any manner as described in this section or elsewhere in this specification, for example by having a particular size and shape, or by comprising a certain volume of foam or other porous material within the cells of the structure. The stabilizing structure or wound closure device may further be altered in any manner described in this section or elsewhere in this specification so as to better accommodate the shape of the wound. After placement in the wound, the stabilizing structure or wound closure device can be sealed by a fluid-tight drape. The fluid-tight drape can comprise a port configured for the application of negative pressure. A source of negative pressure may then be connected to the port and negative pressure may be applied to the wound. The stabilizing structure or wound closure device may be replaced over time by stabilizing structures or wound closure devices of various shapes and sizes as desired to best promote wound healing.

Other Variations

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional or alternative components. These components can include menus, lists, buttons, text boxes, labels, radio buttons, scroll bars, sliders, checkboxes, combo boxes, status bars, dialog boxes, windows, and the like. User interface screens can include additional or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A wound therapy apparatus comprising:
   a negative pressure source configured to provide negative pressure via a fluid flow path to a wound of a patient covered by a wound dressing and to remove fluid from the wound;
   a pressure sensor configured to monitor pressure in the fluid flow path; and
   a controller programmed to:
      monitor a rate of fluid removal from the wound during provision of negative pressure by the negative pressure source by monitoring pressure variations in the fluid flow path using an output of the pressure sensor,
      determine that the rate of fluid removal causes a first volume of fluid being removed from the wound to equal to or exceed a second volume of fluid being provided to the patient, and
      provide a notification responsive to determining that the rate of fluid removal causes the first volume of fluid to equal to or exceed the second volume of fluid.

2. The wound therapy apparatus of claim 1, wherein the controller is further programmed to monitor the rate of fluid removal from a weight of fluid aspirated from the wound.

3. The wound therapy apparatus of claim 1, further comprising a canister configured to store fluid removed from the wound, and wherein the controller is further programmed to monitor the rate of fluid removal based on a level of fluid in the canister.

4. The wound therapy apparatus of claim 3, wherein the controller is further programmed to monitor the level of fluid in the canister using one or more characteristics of pressure in the fluid flow path.

5. The wound therapy apparatus of claim 4, wherein the one or more characteristics of pressure comprises a magnitude of pressure signals, and wherein the magnitude of pressure signals increases as the level of fluid in the canister increases.

6. The wound therapy apparatus of claim 3, wherein the controller is further programmed to monitor the level of fluid in the canister using an activity level of the negative pressure source, and wherein the negative pressure source comprises a vacuum pump and the activity level of the negative pressure source corresponds to a speed of the vacuum pump.

7. The wound therapy apparatus of claim 1, wherein the controller is programmed to determine that the rate of fluid removal causes the first volume of fluid to equal to or exceed the second volume of fluid within a threshold duration following initiation of treating the wound with negative pressure.

8. The wound therapy apparatus of claim 1, wherein the controller is further programmed to cause the negative pressure source to decrease a level of negative pressure provided by the negative pressure source responsive to determining that the rate of fluid removal causes the first volume of fluid to equal to or exceed the second volume of fluid.

9. A kit comprising the wound therapy apparatus of claim 1 and the wound dressing, wherein the wound dressing comprises a stabilizing structure configured to be inserted into the wound, and wherein collapse of the stabilizing structure as a result of provision of negative pressure causes one or more changes of pressure in the fluid flow path.

10. The kit of claim 9, wherein the stabilizing structure is configured to collapse more in a horizontal plane than in a vertical plane perpendicular to the horizontal plane.

11. A method of operating a negative pressure wound therapy apparatus comprising a controller and a negative pressure source configured to provide negative pressure via a fluid flow path to a wound of a patient covered by a wound dressing, the method comprising:
   monitoring a rate of fluid removal from the wound during provision of negative pressure by monitoring pressure variations in the fluid flow path;
   determining that the rate of fluid removal causes a first volume of fluid being removed from the wound to equal to or exceed a second volume of fluid being provided to the patient; and
   providing a notification responsive to determining that the first volume of fluid is equal to or exceeds the second volume,
   wherein the method is performed by the controller.

12. The method of claim 11, further comprising decreasing a level of negative pressure provided by the negative pressure source responsive to determining that the first volume of fluid is equal to or exceeds the second volume.

13. The method of claim 11, wherein monitoring the rate of fluid removal comprises monitoring the rate of fluid removal from a weight of fluid aspirated from the wound.

14. The method of claim 13, wherein monitoring the rate of fluid removal comprises monitoring the weight of fluid aspirated from the wound and a weight of fluid absorbed by the wound dressing or stored in a canister of the negative pressure wound therapy apparatus.

15. The method of claim 11, further comprising monitoring one or more characteristics of pressure in the fluid flow path, and wherein monitoring the rate of fluid removal is performed using the one or more characteristics of pressure.

16. The method of claim 11, wherein monitoring the rate of fluid removal comprises monitoring the rate of fluid removal from a level of fluid in a canister of the negative pressure wound therapy apparatus.

17. The method of claim 16, wherein monitoring the rate of fluid removal comprises monitoring the level of fluid in the canister using one or more characteristics of pressure in the fluid flow path.

18. The method of claim 17, wherein the one or more characteristics of pressure comprises a magnitude of pressure signals, and wherein the magnitude of pressure signals increases as the level of fluid in the canister increases.

19. The method of claim 16, wherein monitoring the rate of fluid removal comprises monitoring the level of fluid in the canister from an activity level of the negative pressure source, and wherein the activity level of the negative pressure source corresponds to a speed of the negative pressure source.

20. The method of claim 11, wherein the wound dressing comprises a stabilizing structure configured to be inserted into the wound, and wherein collapse of the stabilizing structure as a result of provision of negative pressure causes one or more changes of pressure in the fluid flow path.

\* \* \* \* \*